US006211223B1

(12) United States Patent
Challenger et al.

(10) Patent No.: US 6,211,223 B1
(45) Date of Patent: Apr. 3, 2001

(54) INDOLE DERIVATIVES USEFUL IN THERAPY

(75) Inventors: Stephen Challenger; Kevin Neil Dack; Andrew Michael Derrick; Roger Peter Dickinson; David Ellis; Yousef Hajikarimian; Kim James; David James Rawson, all of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/551,779

(22) Filed: Apr. 18, 2000

(30) Foreign Application Priority Data

Oct. 23, 1997 (GB) ................................................ 97222287

(51) Int. Cl.⁷ ........................ A61K 31/404; C07D 405/06
(52) U.S. Cl. ............................................. 514/414; 548/454
(58) Field of Search .............................. 548/454; 514/414

(56) References Cited

FOREIGN PATENT DOCUMENTS

97/43260 11/1997 (WO) .
99/20623 4/1999 (WO) .

OTHER PUBLICATIONS

"Derivados De Indol Util En Terapia"; La Gaceta: Jan. 8, Feb. 8, and Mar. 8, 2000.

*Primary Examiner*—Fiona T. Powers
(74) *Attorney, Agent, or Firm*—Peter C. Richardson; Gregg C. Benson; Carl J. Goddard

(57) ABSTRACT

The invention provides S-(+)-3-{1-(1,3-benzodioxol-5-yl)-2-[(2-methoxy-4-methylphenyl)sulfonylamino]-2-oxoethyl}-1-methyl-1H-indole-6-carboxylic acid, which is substantially free from its (R)-(−)-enantiomer, and pharmaceutically acceptable derivatives thereof. The compounds are useful in the treatment of inter alia acute renal failure, restenosis and pulmonary hypertension.

16 Claims, No Drawings

INDOLE DERIVATIVES USEFUL IN THERAPY

This invention relates to an indole derivative useful in the treatment of a variety of diseases including acute renal failure, restenosis, and pulmonary hypertension, and to pharmaceutical formulations containing the compound.

International Patent Application WO 94/14434 discloses indole derivatives which are indicated as endothelin receptor antagonists. European Patent Application 617001 discloses a large number of phenoxyphenylacetic acid derivatives which are also indicated as endothelin receptor antagonists.

Bergman et al, Tetrahedron, Vol. 31, N° 17, 1975, pages 2063–2073, disclose a number of indole-3-acetic acids. Similar compounds are disclosed by Rusinova et al., Khim. Geterotsikl. Soedin., 1974, (2), 211–213 (see also Chemical Abstracts, Vol. 81, N° 7, Aug. 19, 1974, abstract N° 37455a), and Yarovenko et al, J. Gen. Chem. USSR (English translation), Vol. 39, 1969, page 2039 (see also Beilstein, Registry Number 431619).

These compounds are not indicated in any kind of therapy.

Julian et al., J. Chem. Soc., Chemical Communications, N° 1, 1973, disclose an N-p-chlorobenzoylindole derivative as a by-product of a photo-addition reaction. The compound is not indicated in any kind of therapy.

Yamamoto et al, Japanese Patent N° 70 041 381 (see also Chemical Abstracts, Vol. 75, N° 3, 1971, abstract N° 20189v), disclose an N-p-chlorobenzoylindole derivative which is indicated as an anti-inflammatory agent.

International Patent Application N° PCT/EP97/01882 (filed Apr. 11, 1997, published as WO 97/43260) discloses a group of indole derivatives indicated in the treatment of a variety of diseases including restenosis, renal failure and pulmonary hypertension. Example 17 discloses 3-{1-(1,3-benzodioxol-5-yl)-2-[(2-methoxy-4-methylphenyl)sulfonylamino]-2-oxoethyl}-1-methyl-1H-indole-6-carboxylic acid.

It has now been found that the (+)-enantiomer of 3-{1-(1,3-benzodioxol-5-yl)-2-[(2-methoxy-4-methylphenyl)sulfonylamino]-2-oxoethyl}-1-methyl-1H-indole-6-carboxylic acid possesses significant advantages over the (−)-enantiomer. X-ray studies indicate that the absolute configuration of the (+)-enantiomer of this compound is S.

Thus, according to the present invention, there is provided (S)-(+)-3-{1-(1,3-benzodioxol-5-yl)-2-[(2-methoxy-4-methylphenyl)sulfonylamino]-2-oxoethyl}-1-methyl-1H-indole-6-carboxylic acid,

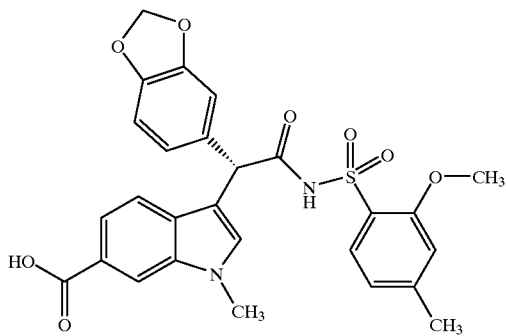

which is substantially free from its (R)-(−)-enantiomer, and pharmaceutically acceptable derivatives thereof (referred to herein as "the compounds of the invention").

In accordance with normal practice, the designation "(+)" indicates that an enantiomer rotates the plane of plane-polarized light in the clockwise direction, for example when in a methanol solution at a concentration of around 1 mg/ml. The designation "(−)" should be construed accordingly.

By "substantially free from its (−)-enantiomer" is meant that a sample of a (+)-enantiomer contains less than 10% by weight of its (−)-enantiomer (i.e. it is more than 90% enantiopure), more preferably less than 5% by weight of its (−)-enantiomer, and most preferably less than 1% by weight of its (−)-enantiomer, for example pure (+)-enantiomer. "Substantially free from its (+)-enantiomer" should be construed accordingly.

Pharmaceutically acceptable derivatives include compounds which are suitable bioprecursors (prodrugs) of (S)-(+)-3-{1-(1,3-benzodioxol-5-yl)-2-[(2-methoxy-4-methylphenyl)sulfonylamino]-2-oxoethyl}-1-methyl-1H-indole-6-carboxylic acid, and pharmaceutically acceptable salts.

Suitable bioprecursors are discussed in Drugs of Today, Vol. 19, 499–538 (1983) and Annual Reports in Medicinal Chemistry, Vol. 10, Ch 31 p306–326, and include $C_{1-6}$ alkyl esters of the carboxylic acid group. Suitable pharmaceutically acceptable salts include alkali metal salts, for example sodium salts.

(S)-(+)-3-{1-(1,3-Benzodioxol-5-yl)-2-[(2-methoxy4-methylphenyl)sulfonylamino]-2-oxoethyl}-1-methyl-1H-indole-6-carboxylic acid may be separated from a racemic mixture using conventional means such as fractional crystallization.

Preferably, the separation is a dynamic resolution. This is possible because the proton attached to the chiral carbon atom is sufficiently acidic to exchange in the presence of base. Thus, the acid in solution epimerizes throughout the process, but the desired diastereomeric salt precipitates during the process, leaving a diminishing quantity of the unwanted enantiomer in solution. In this process the theoretical yield of the desired enantiomer is 100%, whereas conventional fractional crystallization can only yield a maximum of 50% of the desired enantiomer. Thus, according to a further aspect of the present invention, there is provided a process for the production of (S)-(+)-3-{1-(1,3-benzodioxol-5-yl)-2-[(2-methoxy-4-methylphenyl)sulfonylamino]-2-oxoethyl}-1-methyl-1H-indole-6-carboxylic acid as defined above, or a pharmaceutically acceptable derivative thereof, which comprises selective precipitation from a solution of 3-{1-(1,3-benzodioxol-5-yl)-2-[(2-methoxy-4-methylphenyl)sulfonylamino]-2-oxoethyl}-1-methyl-1H-indole-6-carboxylic acid of a diastereomeric salt formed between (S)-(+)-3-{1-(1,3-benzodioxol-5-yl)-2-[(2-methoxy-4-methylphenyl)sulfonylamino]-2-oxoethyl}-1-methyl-1H-indole-6-carboxylic acid and a chiral base.

Preferably, the chiral base is (S)-(−)-α-methylbenzylamine.

Preferably, the solvent is a mixture of tetrahydrofuran and 1,2-dimethoxyethane, for example an approximately 1:1 mixture by volume, such as 9:11.

Preferably, the diastereomeric salt is formed by mixing the acid with the base in a molar ratio in the range 1:1.5 to 1:2.5.

Preferably, the temperature is initially in the range 55–60° C., and then reduced to 45° C. Preferably, the temperature reaches 45° C. 3 days after beginning the process.

Preferably, 10 ml of solvent is used for every gram of acid present.

Preferably, the reaction mixture is seeded with the desired diastereomeric salt, preferably at the beginning of the process. This can be obtained from a different synthetic route initially, but can be obtained from a previous batch of product when the process is run repeatedly.

The dynamic resolution described above can produce compound of sufficiently high enantiopurity for use in the clinic. However, the enantiopurity can be increased still further by preparing the disodium salt, crystallizing it, and converting it back to the free acid.

Alternatively, (S)-(+)-3-{1-(1,3-benzodioxol-5-yl)-2-[(2-methoxy-4-methylphenyl)-sulfonylamino]-2-oxoethyl}-1-methyl-1H-indole-6-carboxylic acid may be prepared according to Scheme 1 (described more fully in Example 1 below):

Scheme 1

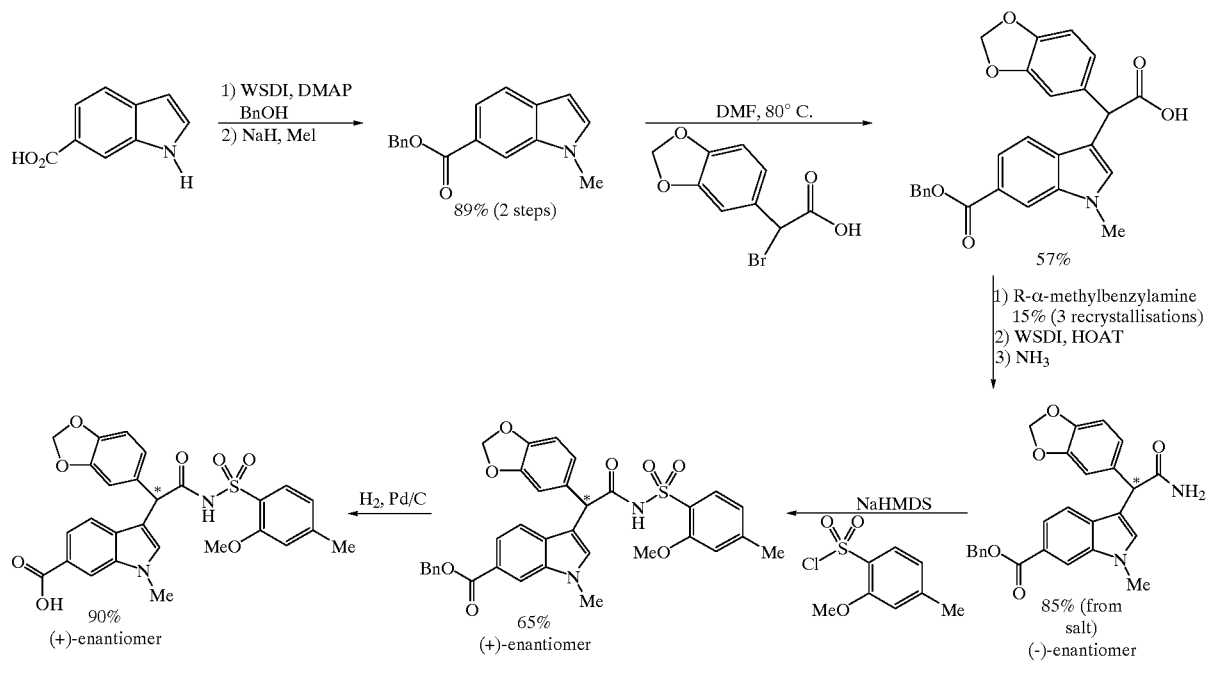

In International Patent Application WO 97/43260, Example 17 is prepared according to Scheme 2 below:

Scheme 2

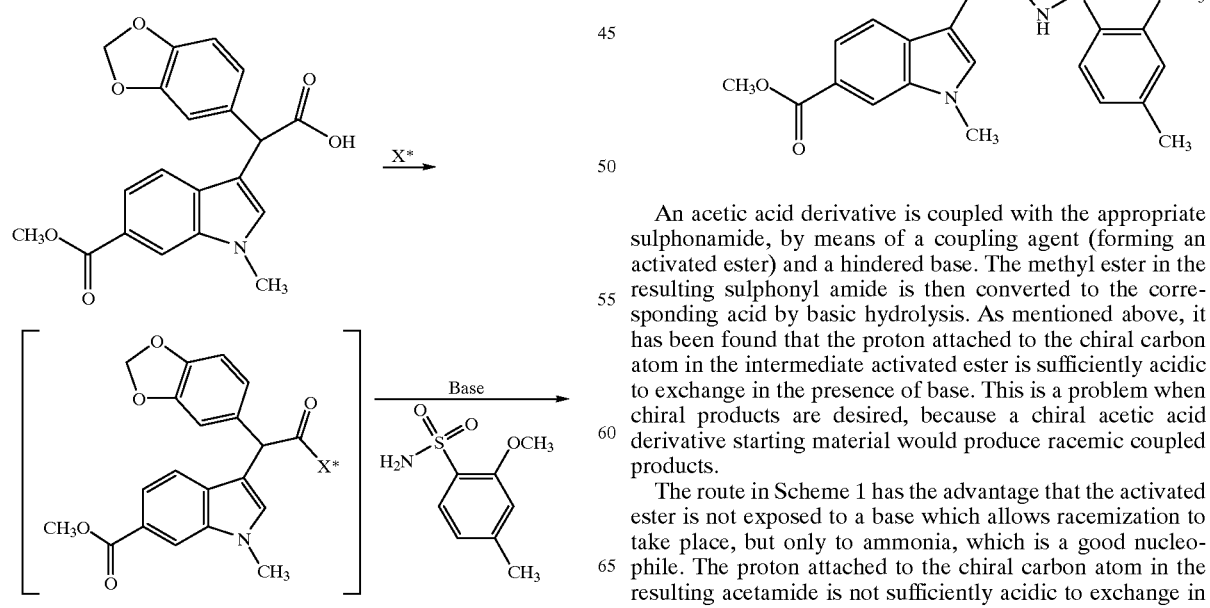

An acetic acid derivative is coupled with the appropriate sulphonamide, by means of a coupling agent (forming an activated ester) and a hindered base. The methyl ester in the resulting sulphonyl amide is then converted to the corresponding acid by basic hydrolysis. As mentioned above, it has been found that the proton attached to the chiral carbon atom in the intermediate activated ester is sufficiently acidic to exchange in the presence of base. This is a problem when chiral products are desired, because a chiral acetic acid derivative starting material would produce racemic coupled products.

The route in Scheme 1 has the advantage that the activated ester is not exposed to a base which allows racemization to take place, but only to ammonia, which is a good nucleophile. The proton attached to the chiral carbon atom in the resulting acetamide is not sufficiently acidic to exchange in the presence of base, and so reaction with the appropriate sulphonyl chloride in the presence of a hindered base leads to chiral products. The benzyl protecting group is then removed by catalytic hydrogenation.

Thus, according to the invention, there is further provided a process for the production of the compounds of the invention, which comprises removing the protecting group from the (+)-enantiomer of a compound of formula I, which is substantially free from its (−)-enantiomer,

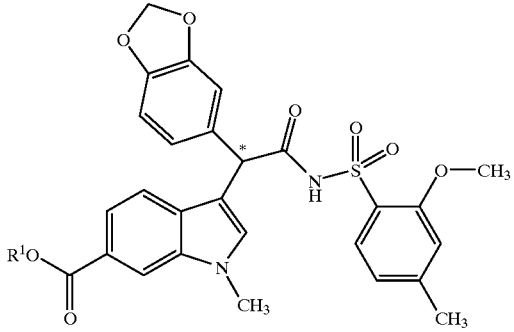

I wherein $R^1$ represents a carboxylic acid protecting group.

Suitable protecting groups include benzyl, which may be removed by catalytic hydrogenation.

The invention further provides a process for producing the (+)-enantiomer of a compound of formula I, which comprises reacting 2-methoxy-4-methylbenzenesulfonyl chloride with the (−)-enantiomer of a compound of formula II, which is substantially free from its (+)-enantiomer,

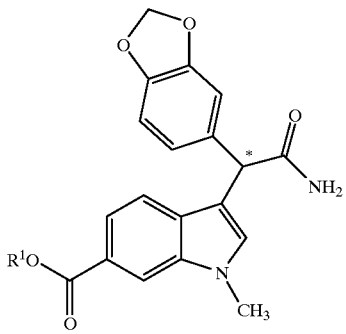

II wherein $R^1$ is as defined above.

The above intermediates (namely the (+)-enantiomers of compounds of formula I and the (−)-enantiomers of compounds of formula II) are also provided by the invention.

The compounds of the invention are useful because they have pharmacological activity in animals, including humans. More particularly, they are useful in the treatment of acute renal failure, restenosis, pulmonary hypertension, benign prostatic hypertrophy, congestive heart failure, stroke, angina, atherosclerosis, cerebral and cardiac ischaemia and cyclosporin induced nephrotoxicity. The treatment of acute renal failure, restenosis and pulmonary hypertension are of particular interest. The compounds of the invention may be administered alone or as part of a combination therapy.

Thus, according to a further aspect of the invention, there is provided a compound of the invention, for use as a pharmaceutical.

There is further provided a pharmaceutical formulation comprising a compound of the invention, and a pharmaceutically acceptable adjuvant, diluent or carrier.

The invention also provides the use of the compounds of the invention in the manufacture of a medicament for the treatment of acute renal failure, restenosis, pulmonary hypertension, benign prostatic hypertrophy, congestive heart failure, stroke, angina, atherosclerosis, cerebral and cardiac ischaemia or cyclosporin induced nephrotoxicity. The invention also provides a method of treatment of these diseases, which comprises administering a therapeutically effective amount of a compound of the invention to a patient in need of such treatment.

The compounds of the invention may also be useful in the treatment of animals such as companion animals, for example dogs and cats.

Without being limited by theory, the compounds of the invention are believed to be endothelin receptor antagonists. Endothelin (ET) is a potent vasoconstrictor synthesised and released by endothelial cells. There are three distinct isoforms of ET: ET-1, ET-2 and ET-3, all being 21-amino acid peptides and herein the term 'endothelin' refers to any or all of the isoforms. Two receptor subtypes, $ET_A$ and $ET_B$ have been pharmacologically defined (see for example H. Arai et al, Nature, 348, 730, 1990) and further subtypes have recently been reported. Stimulation of $ET_A$ promotes vasoconstriction and stimulation of $ET_B$ receptors causes either vasodilation or vasoconstriction.

The effects of endothelin are often long-lasting and, as the endothelins are widely distributed in mammalian tissues, a wide range of biological responses has been observed in both vascular and non-vascular tissue. The main effects of endothelin are observed in the cardiovascular system, particularly in the coronary, renal, cerebral and mesenteric circulation.

Increased circulating levels of endothelin have been observed in patients who have undergone percutaneous transluminal coronary angioplasty (PTCA) (A. Tahara et al, Metab. Clin. Exp. 40, 1235, 1991) and ET-1 has been found to induce neointimal formation in rats after balloon angioplasty (S. Douglas et al, J.Cardiovasc.Pharm., 22 (Suppl 8), 371, 1993). The same workers have found that an endothelin antagonist, SB-209670, causes a 50% reduction in neointimal formation relative to control animals (S. Douglas et al, Circ Res, 75, 1994). Antagonists of the endothelin receptor may thus be useful in preventing restenosis post PTCA.

Endothelin-1 is produced in the human prostate gland and endothelin receptors have been identified in this tissue. Since endothelin is a contractile and proliferative agent endothelin antagonists could be useful in the treatment of benign prostate hypertrophy.

There is widespread localisation of endothelin and its receptors in the central nervous system and cerebrovascular system (R. K. Nikolov et al, Drugs of Today, 28(5), 303, 1992) with ET being implicated in cerebral vasospasm, cerebral infarcts and neuronal death. Elevated levels of endothelin have also been observed in patients with:

Chronic renal failure (F. Stockenhuber et al, Clin Sci (Lond.), 82, 255, 1992)

Ischaemic Heart Disease (M. Yasuda, Am. Heart J., 119, 801, 1990)

Stable or unstable angina (J. T. Stewart, Br. Heart J. 66, 7 1991)

Pulmonary Hypertension (D. J. Stewart et al, Ann. Internal Medicine, 114, 464, 1991)

Congestive heart failure (R. J. Rodeheffer et al, Am.J.Hypertension, 4, 9A, 1991)

Preeclamnpsia (B. A. Clark et al, Am.J.Obstet.Gynecol., 166, 962, 1992)

Diabetes (A. Collier et al, Diabetes Care, 15 (8), 1038, 1992)

Crohn's disease (S. H. Murch et al, Lancet, 339, 381, 1992)

Atherosclerosis (A. Lerman et al, New Eng. J. Med., 325, 997, 1991)

In every case, the disease state associated with the physiologically elevated levels of endothelin is potentially treatable with an endothelin receptor antagonist and hence a compound of the invention.

Compounds that selectively antagonise the $ET_A$ receptor rather than the $ET_B$ receptor are preferred.

The biological activity of the compounds of the invention may be demonstrated in Tests A–C below:

A. Binding Assay

Competition between test compounds and $^{125}$I-ET-1 binding to human endothelin receptors is determined as follows.

Binding to $ET_A$ Receptors

25 μl of a 30 pM solution of $[^{125}I]Tyr^{13}$ ET-1 (specific activity 2,200 Ci/mM) is mixed with 25 μl samples of test compound (final concentrations in the range 0.1 nM–50,000 nM). 200 μl of a solution containing cloned human $ET_A$ receptor (0.75 pmoles receptor protein/ml), 50 mM Tris, 0.5 mM $CaCl_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radioactivity, and the $IC_{50}$ (the concentration of test compound at which 50% of the radiolabelled compound is unbound) determined for the concentration range tested.

Binding to $ET_B$ Receptors

25 μl of a 30 pM solution of $[^{125}I]Tyr^{13}$ ET-1 (specific activity 2,200 Ci/mM) is mixed with 25 μl samples of test compound (final concentrations 0.1 nM–50,000 nM). 200 μl of a solution containing cloned human $ET_B$ receptor (0.25 pmoles receptor protein/ml), 50 mM Tris, 0.5 mM $CaCl_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radioactivity, and the $IC_{50}$ (the concentration of test compound at which 50% of the radiolabelled compound is unbound) determined for the concentration range tested.

B. In Vitro Vascular Smooth Muscle Activity

Rat Aorta

Rat aortae are cleaned of connective tissue and fat and cut into helical strips approximately 4 mm in width. The endothelium is removed by dragging the luminal surface of the tissue gently across filter paper moistened with Krebs solution of composition (mM) NaCl 130, KCl 5.6, $NaHCO_3$ 25, Glucose 11.1, $NaH_2PO_4$ 0.6, $CaCl_2$ 2.16, $MgCl_2$ 0.5, gassed with 95% $O_2$/5% $CO_2$. The strips are mounted in isolated organ baths in Krebs solution under a resting tension of I gram. Organ bath solutions are maintained at 37° C. and continuously aerated with 95% $O_2$/5% $CO_2$. Tensions are measured with Maywood Industries isometric force transducers and displayed on Gould TA4000 recorders. After equilibration in the organ bath for 1 hour, tissues are contracted by the addition of KCl to a final concentration of 60 mM. The KCl is removed by replacing the Krebs solution, with two further washes with Krebs solution. To determine the potency of an $ET_A$ receptor antagonist, two tissues are cumulatively dosed with ET-1 (0.1 nM–1 μM); other tissues are dosed with ET-1 (0.1 nM–1 μM) in duplicate, beginning 30 minutes after the inclusion in the organ bath medium of the test compound. Sufficient tissues are used per experiment to generate dose-response curves to ET-1 in the absence and the presence of at least 3 concentrations of antagonist. Data are expressed as the mean±s.e.m. Dissociation constants ($k_b$) of competitive antagonists are calculated by the method of Arunlakshana and Schild.

Rabbit Pulmonary Artery

Isolated rabbit pulmonary arteries are cleaned of connective tissue and fat and cut into rings approximately 4 mm in width. The endothelium is removed by inserting a fibrous instrument moistened with Krebs solution of composition (mM) NaCl 130, KCl 5.6, $NaHCO_3$ 25, Glucose 11.1, $NaH_2PO_4$ 0.6, $CaCl_2$ 2.16, $MgCl_2$ 0.5, gassed with 95% $O_2$/5% $CO_2$. The rings are mounted in isolated organ baths in Krebs solution under a resting tension of 1 gram. Organ bath solutions are maintained at 37° C. and continuously aerated with 95% $O_2$/5% $CO_2$. Tensions are measured with Maywood Industries isometric force transducers and displayed on Gould TA4000 recorders. After equilibration in the organ bath for 1 hour, tissues are contracted by the addition of KCl to a final concentration of 60 mM. The KCl is removed by replacing the Krebs solution, with two further washes with Krebs solution. To determine the potency of an $ET_B$ receptor antagonist, two tissues are cumulatively treated with BQ-3020 (0.1 nM–1 μM; other tissues are treated with BQ-3020 (0.1 nM–1 μM) in duplicate, beginning 30 minutes after the inclusion in the organ bath medium of the test compound. Sufficient tissues are used per experiment to generate dose-response curves to BQ-3020 in the absence and the presence of at least 3 concentrations of antagonist. Data are expressed as the mean∓s.e.m. Dissociation constants ($k_b$) of competitive antagonists are calculated by the method of Arunlakshana and Schild.

C. In Vivo Blockade of Endothelin-induced Blood Pressure Elevation

In anaesthetised, ganglion-blocked and artificially respired rats, the left common carotid artery and the right jugular vein are cannulated for the measurement of arterial blood pressure and the administration of compound respectively. Rats are treated with the $ET_B$ antagonist BQ-788 (0.25 mg/kg i.v.). Beginning 10 minutes after administering BQ-788, the hypertensive response to ET-1 (1 μg/kg i.v.) is determined. When the blood pressure has returned to baseline, the test compound is administered (0.1–20 mg/kg i.v.) and after 10 minutes the ET-1 challenge is repeated. Increasing concentrations of the test compound are administered, followed 10 minutes after each administration by a further ET-1 challenge. An $IC_{50}$ is determined based upon inhibition of ET-1 induced pressor response upon cumulative dosing with compound.

Duration of blockade is determined in anaesthetised, ganglion-blocked and artificially respired rats, in which the left common carotid artery and the right jugular vein are cannulated for the measurement of arterial blood pressure and the administration of compound respectively. Rats are treated with the $ET_B$ antagonist BQ-788 (0.25 mg/kg i.v.). Beginning 10 minutes after administering BQ-788, the hypertensive response to ET-1 (1 μg/kg i.v.) is determined. When the blood pressure has returned to baseline, the test compound is administered (10 mg/kg i.v.). Further administrations of ET-1 are made 5, 20 and 60 minutes after dosing the test compound. In separate animals, prepared similarly, an ET-1 challenge is made 2 or 4 hours after dosing with the test compound, in these animals BQ-788 is dosed 10 minutes before the ET-1 challenge. For later time points, rats are dosed with the test compound (10 mg/kg) i.v. via a tail vein or p.o., they are then anaesthetised and prepared for blood pressure measurement as above. In these rats, ET-1 (1 μg/kg i.v.) was administered 6 or 8 hours after the test compound.

For human use, the compounds of the invention can be administered alone but will generally be administered in admixture with a pharmaceutical carrier selected with regard to the intended route of administration and standard pharmaceutical practice. For example they can be administered orally in the form of tablets containing such excipients as starch or lactose or in capsules or ovules either alone or in admixture with excipients or in the form of elixirs, solutions or suspensions containing the compound in a liquid carrier, for example a vegetable oil, glycerine or water with a flavouring or colouring agent. They can be injected parenterally, for example intravenously, intramuscularly or subcutaneously. For parental administration, they are best used as sterile aqueous solutions which may contain other substances, for example, enough glucose or salts to make the solution isotonic with blood. For parenteral administration the compound may also be administered as a solution or suspension in a suitable oil, for example polyethylene glycol, lecithin or sesame oil. Intravenous administration of the free acid is of particular interest.

Compounds of the invention may also be administered through inhalation of a solution, suspension or emulsion that may be administered as a dry powder or in the form of an aerosol using a conventional propellant such as dichlorodifluoromethane.

For oral or parenteral administration to human patients the daily dosage levels of compounds of the invention will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. For an average adult, an intravenous bolus dose could contain 40 mg of the drug, and a continuous intravenous infusion could deliver 30 mg/day. The above dosages are, of course only exemplary of the average case and there may be instances where higher or lower doses are merited, and such are within the scope of the invention.

Alternatively, the compounds of the invention can be administered in the form of a suppository or pessary, or they may be applied topically in the form of a lotion, solution, cream, ointment or dusting powder or in the form of a medicated plaster, patch or membrane. For example they may be incorporated in a cream containing an aqueous emulsion of polyethylene glycols or liquid paraffin. The compounds may also be administered intranasally.

The compounds of the invention have the advantage that they have a high affinity for the $ET_A$ receptor, and that they are selective for the $ET_A$ receptor over the $ET_B$ receptor. Thus they are likely to be potent in the treatment of disorders in which increased levels of circulating endothelin are implicated, and to have reduced side effects. They also have a longer duration of action and a higher solubility than the compounds of the prior art.

The invention is illustrated by the following Examples, in which the following abbreviations are used:
APCI atmospheric pressure chemical ionization
DSC differential scanning calorimetry
ee enantiomeric excess
h hour
HPLC high performance liquid chromatography
LRMS low resolution mass spectroscopy
min minute
NMR nuclear magnetic resonance
psi pounds per square inch
THF tetrahydrofuran

EXAMPLE 1

(S)-(+)-3-{1-(1,3-Benzodioxol-5-yl)-2-[(2-methoxy-4-methylphenyl)sulfonylamino]-2-oxoethyl)-1-methyl}-1H-indole-6-carboxylic acid (a) Benzyl 1H-indole-6-carboxylate

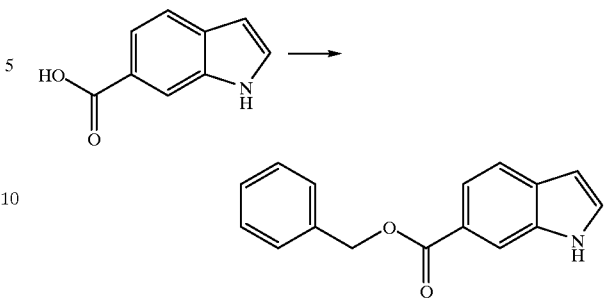

1-(3-Dimethylaminopropyl)-3-ethylcarbodiimide hydrochloride (5 g, 26.1 mmol) was added to a stirred solution of benzyl alcohol (2.47 ml, 23.9 mmol), 1H-indole-6-carboxylic acid (3.5 g, 21.7 mmol) and N,N-dimethylaminopyridine (3.4 g, 28.3 mmol) in dichloromethane (40 ml) at room temperature under a nitrogen atmosphere. After 12 h the reaction mixture was poured into 1M hydrochloric acid (200 ml) and extracted with dichloromethane (2×200 ml). The combined organics were dried (MgSO$_4$) and concentrated to give a brown oil. Flash column chromatography (elution with dichloromethane) gave the subtitle compound (5.4 g).

$^1$H NMR (400 MHz, CDCl$_3$) δ: 5.40 (s, 2H), 6.60 (s, 1H), 7.30–7.50 (m, 6H), 7.60 (d, 1H), 7.80 (d, 1H), 8.20 (s, 1H), 8.40 (brs, 1H). LRMS (Thermospray): 252.1 (MH$^+$)

(b) Benzyl 1-methyl-1H-indole-6carboxylate

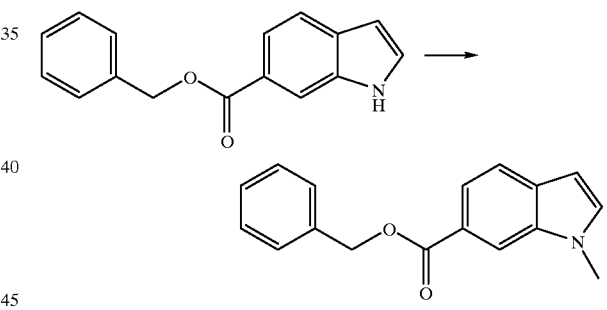

Sodium hydride (1.03 g of a 60% dispersion in paraffin oil) was added portionwise to a stirred solution of benzyl 1H-indole-6-carboxylate (from (a), 5.4 g, 21.5 mmol) in tetrahydrofuran (80 ml) at 0° C. under a nitrogen atmosphere. The mixture was stirred for 2 h, then methyl iodide (2.04 ml, 32.6 mmol) was added dropwise. The solution was allowed to warm to room temperature over 12 h. The reaction was quenched by the slow addition of ice cold water and the tetrahydrofuran was removed in vacuo. The product was extracted from saturated sodium chloride solution (300 ml) with dichloromethane (2×300 ml) and the organics were dried (MgSO$_4$). The dried organics were filtered through a 5 cm plug of silica in a sintered funnel and concentrated in vacuo to give the subtitle compound as a white solid (5.1 g).

$^1$H NMR (400 MHz, CDCl$_3$) δ: 3.80 (s, 3H), 5.40 (s, 2H), 6.50 (s, 1H), 7.20 (s, 1H), 7.30–7.50 (m, 5H), 7.60 (d, 1H), 7.80 (d, 1H), 8.10 (s, 1H). LRMS (Thermospray): 266.1 (MH$^+$)

(c) 2-(1,3-Benzodioxol-5-yl)-2-[6-(benzyloxy)carbonyl-1-methyl-1H-indol-3-yl]acetic acid

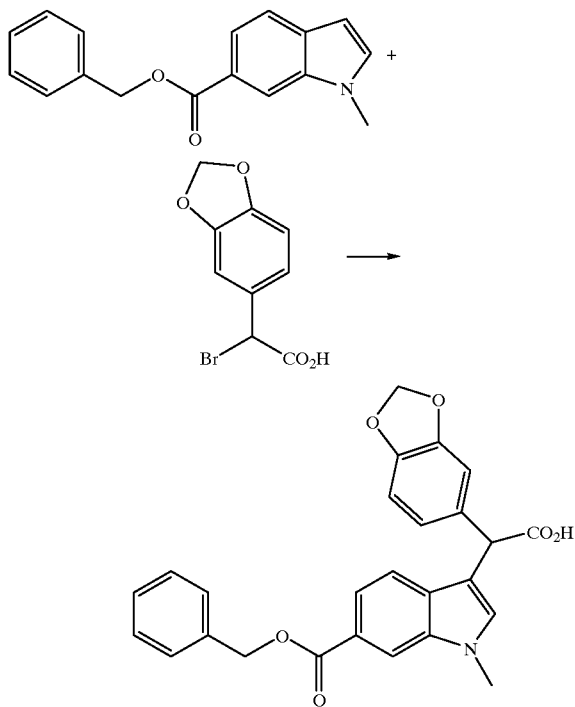

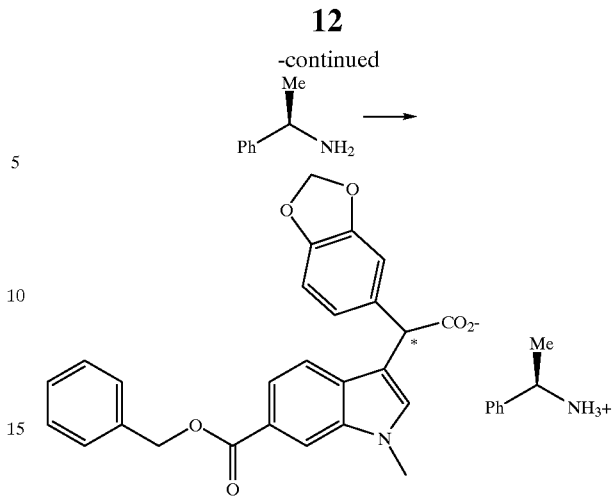

Benzyl 1-methyl-1H-indole-6-carboxylate (from (b), 9.8 g) and 2-(1,3-benzodioxol-5-yl)-2-bromoacetic acid (from Preparation 1, 10.5 g) were stirred together in dimethylformamide (100 ml) and a steady stream of nitrogen was passed through the solution which was warmed to 90° C. After 4 h the reaction mixture was cooled to room temperature and the dimethylformamide removed in vacuo. The oily residue was partitioned between ethyl acetate (300 ml) and 2M hydrochloric acid and the organic phase was washed with more 2M hydrochloric acid (3×50 ml) and brine (50 ml). The organic phase was dried (MgSO$_4$) and decolourising charcoal was added. The slurry was filtered and concentrated to give an orange oil. Flash column chromatography (gradient elution from 100% CH$_2$Cl$_2$ to 95% CH$_2$Cl$_2$/5% MeOH) gave 9.97 g of the subtitle compound.

$^1$H NMR (400 MHz, CDCl$_3$) δ: 3.80 (s, 3H), 5.10 (s, 1H), 5.40 (s, 2H), 5.90 (s, 2H), 6.70 (d, 1H), 6.80 (d, 1H), 6.85 (s, 1H), 7.20–7.40 (m, 7H), 7.70 (d, 1H), 8.00 (s, 1H). LRMS (APCI): 445.4 (MH$^+$).

(d) 2-(1,3-Benzodioxol-5-yl)-2-[6-(benzyloxy)carbonyl-1-methyl-1H-indol-3-yl]acetic acid, R-(α)-methylbenzylamine salt

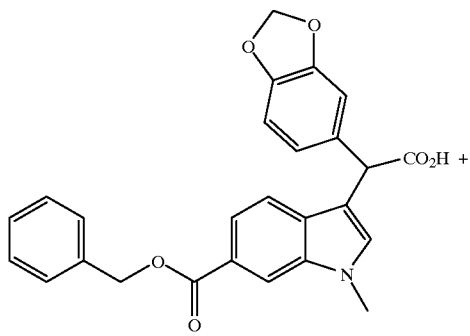

R-(α)-methylbenzylamine (2.72 g) and 2-(1,3-benzodioxol-5-yl)-2-[6-(benzyloxy)carbonyl-1-methyl-1H-indol-3-yl]acetic acid (from (c), 9.97 g) were dissolved in hot ethyl acetate (1 liter). Recrystallisation of the salt (three times from ethyl acetate) gave the subtitle compound as a white crystalline solid (2.7 g). The enantiomeric excess of the salt was found to be >98% using chiral stationary phase HPLC.

$^1$H NMR (400 MHz, d$_6$-DMSO) δ: 1.25 (d, 3H), 3.80 (s, 3H), 4.05 (q, 1H), 4.95 (s, 1H), 5.30 (s, 2H), 5.90 (d, 214) 6.70 (d, 1H), 6.80 (d, 1H), 6.90 (s, 1H), 7.20–7.50 (m, 12H), 7.60 (d, 1H), 8.00 (s, 1H). LRMS (APCI): 444.6 (MH$^+$). Analysis: found C, 71.95; H, 5.65; N, 4.92; C$_{34}$H$_{32}$N$_2$O$_6$ requires C, 72.32; H, 5.71; N, 4.96.

(e) (–)-Benzyl 3-[2-amino-1-(1,3-benzodioxol-5-yl)-2-oxoethyl]-1-methyl-1H-indole-6-carboxylate

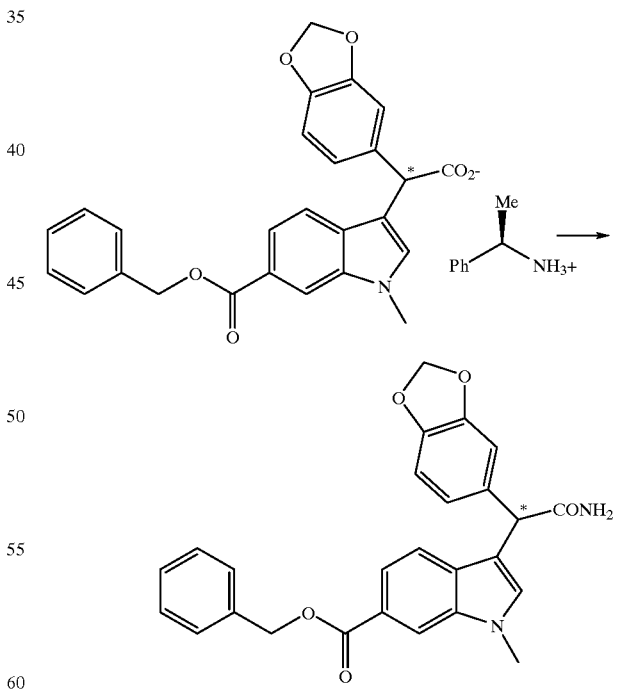

The R-(α)-methylbenzylamine salt of 2-(1,3-benzodioxol-5-yl)-2-[6-(benzyloxy)carbonyl-1-methyl-1H-indol-3-yl]acetic acid (from (d), 2.7 g) was extracted from 2M hydrochloric acid with ethyl acetate, and the ethyl acetate was washed with 2 further portions of 2M hydrochloric acid and brine before drying (MgSO$_4$), filtering and concentrating in vacuo. The resulting foam was dissolved in dichloromethane (25 ml) and treated sequentially with hydroxyazabenzotriazole (850 mg), and 1-(3-dimethylaminopropyl)-3-ethylcarbodiimide hydrochloride (1.4 g). After 90 minutes the solution was washed with aqueous citric acid (3×25 ml) and brine (25 ml) and the dichloromethane dried (MgSO$_4$) and filtered. The filtrate was cooled in an ice bath and treated with 0.88M ammonia solution (0.7 ml). After 15 min the solvent and excess ammonia were evaporated and the residue was partitioned between ethyl acetate and aqueous citric acid. An insoluble white precipitate (desired product) was filtered and the organic layer was separated. The organic layer was then washed with aqueous citric acid, aqueous saturated sodium bicarbonate solution and brine, dried (MgSO$_4$) and concentrated to give a white solid. This was combined with the white solid filtered off earlier and azeotroped with dichloromethane. Combined yield of the subtitle compound was 84% (1.78 g). Chiral stationary phase HPLC showed that the chiral integrity had been maintained (still >98%ee).

$^1$H NMR (400 MHz, d$_6$-DMSO) δ: 3.80 (s, 3H), 5.00 (s, 1H), 5.33 (s, 2H), 5.90 (d, 2H), 6.75 (d, 1H), 6.80 (d, 1H), 6.88 (s, 1H), 6.95 (s, 1H), 7.20–7.60 (m, 9H), 8.00 (s, 1H). LRMS (Thermospray): 443.0 (MH$^+$). Analysis: found C, 70.11; H, 4.96; N, 6.29; C$_{26}$H$_{22}$N$_2$O$_5$ requires C, 70.57; H, 5.01; N, 6.33.

(f) (+)-Benzyl 3-{(1-(1,3-benzodioxol-5-yl)2-[(2-methoxy-4-methylphenyl)sulfonyl-amino]-2-oxoethyl}-1-methyl-1H-indole-6-carboxylate

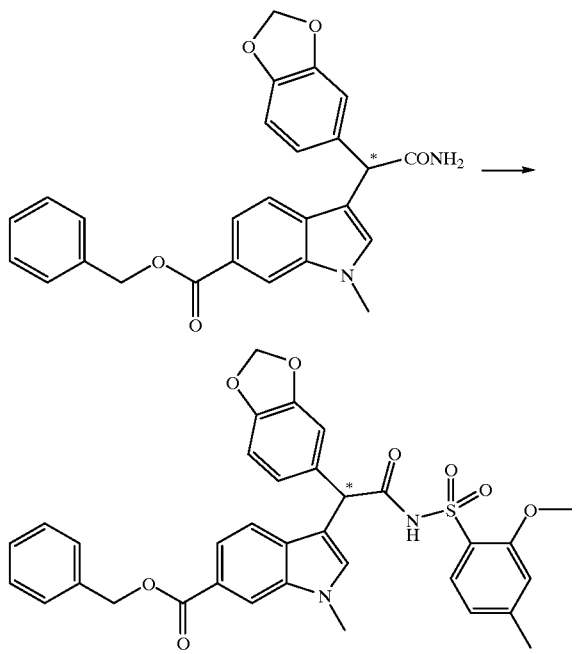

(−)-Benzyl 3-[2-amino-1-(1,3-benzodioxol-5-yl)-2-oxoethyl]-1-methyl-1H-indole-6-carboxylate (from (e), 500 mg) was dissolved in dry tetrahydrofuran (12 ml) under a nitrogen atmosphere. The solution was cooled to −60° C. and sodium hexamethyldisilazide (1.13 ml of a 1M solution in THF) was added over 1–2 minutes. The resulting pale yellow solution was allowed to warm to −40° C. and a solution of the sulphonyl chloride (from Preparation 2, 250 mg) in tetrahydrofuran (0.5 ml) was added over 2 minutes. After 20 minutes the solution was recooled to −60° C. and a further 0.6 ml of sodium hexamethyldisilazide (1.13 ml of a 1M solution in THF) was added. After 20 minutes the solution was warmed to −40° C. and a further solution of the sulphonyl chloride (from (f), 250 mg) in tetrahydrofuran (0.5 ml) was added. After 30 minutes the reaction was quenched by the addition of aqueous NH$_4$Cl (5 ml) and allowed to warm to room temperature. The mixture was diluted with ethyl acetate and washed with 1M hydrochloric acid followed by saturated sodium chloride solution. The organics were separated, dried (MgSO$_4$) and concentrated. Flash column chromatography (gradual gradient elution starting with dichloromethane and ending with 95% dichloromethane/5% methanol) gave the subtitle compound (390 mg).

$^1$H NMR (400 MHz, CDCl$_3$) δ: 2.40 (s, 3H), 3.40 (s, 3H), 3.75 (s, 3H), 5.00 (s, 1H), 5.40 (s, 2H), 5.90 (s, 2H), 6.60 (s, 1H), 6.70 (s, 3H), 6.80 (d, 1H), 7.00 (s, 1H), 7.20 (d, 1H), 7.30–7.50 (m, 5H), 7.60 (d, 1H), 7.90 (d, 1H), 8.00 (s, 1H), 8.80 (brs, 1H). LRMS (Thermospray): 644.7 (MNH$_4^+$). Analysis: found C, 63.66; H, 4.71; N, 4.33; C$_{34}$H$_{30}$N$_2$O$_8$.0.25 CH$_2$Cl$_2$ requires C, 63.49; H, 4.74; N, 4.32.

[α]$_D$=+32.3° (λ=436 nm) (c=1 mg/ml, methanol)

(g) (S)-(+)-3-{1-(1,3-Benzodioxol-5-yl)-2-[(2-methoxy-4-methylphenyl)sulfonyl-amino]-2-oxoethyl}-1-methyl-1H-indole-6-carboxylic acid

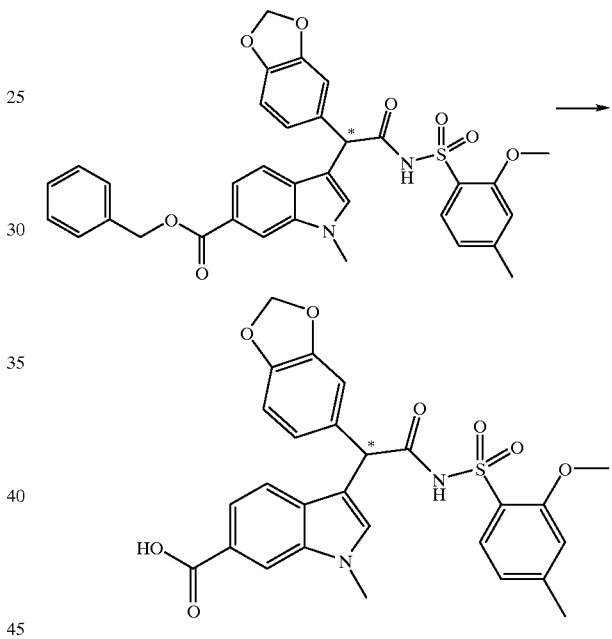

(+)-Benzyl 3-{1-(1,3-benzodioxol-5-yl)-2-[(2-methoxy-4-methylphenyl)sulfonylamino]-2-oxoethyl}-1-methyl-1H-indole-6-carboxylate (from (f), 374 mg) was dissolved in aqueous ethanol (20 ml of 9:1 ethanol/water) and 50 mg of 5% palladium on carbon was added. After 3 h at 414 kPa (60 psi) of hydrogen at room temperature a further 50 mg of catalyst was added and the hydrogenation continued for a further 3 h. The catalyst was removed by filtration and the filtrate evaporated. The residue was azeotroped several times with dichloromethane to give the title compound (290 mg) in >98%ee (determined by chiral HPLC).

$^1$H NMR (400 MHz, d$_6$-DMSO): δ2.30 (s, 3H), 3.60 (s, 3H), 3.70 (s, 3H), 5.20 (s, 1H), 5.90 (2H, d), 6.65 (d, 1H), 6.70 (s, 1H), 6.80 (d, 1H), 6.85 (d, 1H), 6.90 (s, 1H), 7.10 (s, 1H), 7.25 (d, 1H), 7.50 (d, 1H), 7.60 (d, 1H), 8.00 (s, 1H), 12.25 (brs, 1H), 12.50 (brs, 1H). LRMS (Thermospray): 537.5 (MH$^+$). Analysis: found C, 54.67; H, 4.18; N, 4.53; C$_{27}$H$_{24}$N$_2$O$_8$S.CH$_2$Cl$_2$ requires C, 54.11; H, 4.22;N,4.51.

[α]$_D$=+23.40° (λ=436 nm) (c=1.07 mg/ml, methanol)

EXAMPLE 2

(S)-(+)-3-{1-(1,3-Benzodioxol-5-yl)-2-[(2-methoxy-4-methylphenyl)sulfonylamino]-2-oxoethyl}-1-methyl-1H-indole-6-carboxylic acid (alternative route)

(a) 2-(1,3-Benzodioxol-5-yl)-2-(6-methoxycarbonyl-1-methyl-1H-indol-3-yl)acetic acid

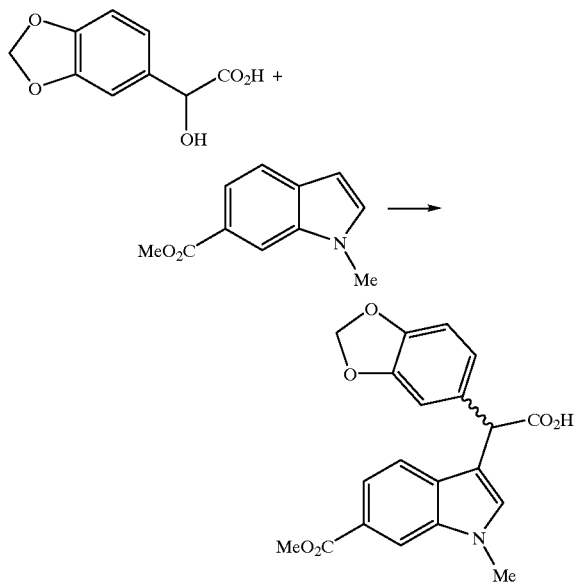

Trifluoroacetic acid (1.92 kg) was added portionwise to a stirred suspension of methyl 1-methyl-1H-indole-6-carboxylate (prepared by the same method as 1-methylindole-6-tert-butyl ester in Example 28, International Patent Application WO 97/43260, but using methanol in place of 6-tert-butanol; 1.63 kg) and 2-(1,3-benzodioxol-5-yl)-2-hydroxyacetic acid (1.67 kg) in acetonitrile (16.3 liters) at room temperature under a nitrogen atmosphere. The suspension was heated to reflux for 24 h and allowed to cool to room temperature. Filtration of the precipitated product gave the subtitle compound as a white crystalline solid (2.54 kg, 80.4%).

m.p.194–198° C. $^1$H NMR (300 MHz, CDCl$_3$) δ: 3.83 (s, 3H), 3.94 (s, 3H), 5.19 (s, 1H), 5.93 (s, 2H), 6.76 (d, 1H), 6.87–6.90 (m, 2H), 7.26 (s, 1H), 7.44 (d, 1H), 7.76 (d, 1H), 8.07 (s, 1H) LRMS: 368.0 (MH$^+$) Analysis: found C, 65.34; H, 4.61; N, 3.81; C$_{20}$H$_{17}$NO$_6$ requires C, 65.39; H, 4.66; N, 3.81%

(b) Methyl 3-{1-(1,3-benzodioxol-5-yl)-2-[(2-methoxy-4-methylphenyl)sulfonyl-amino]-2-oxoethyl}-1-methyl-1H-indole-6-carboxylate

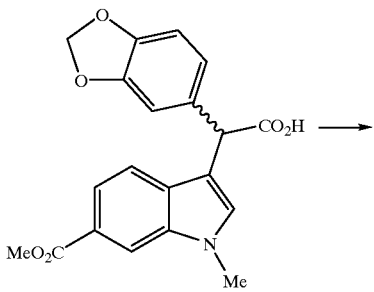

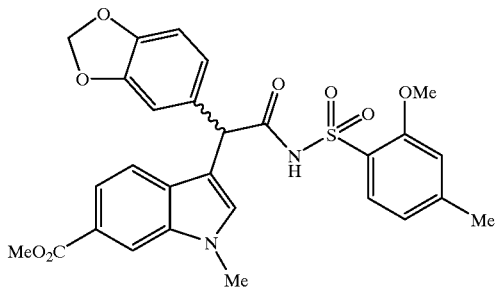

1,1'-Carbonyldiimidazole (2.8 kg) was added to a stirred solution of 2-(1,3-benzodioxol-5-yl)-2-(6-methoxycarbonyl-1-methyl-1H-indol-3-yl)acetic acid (from step (a), 5.0 kg) in dry tetrahydrofuran (50 liters) at room temperature under a nitrogen atmosphere. The suspension was heated to reflux for 1.5 h, allowed to cool to room temperature, and treated sequentially with 2-methoxy-4-methylbenzenesulfonamide (see Preparation 11, International Patent Application WO 97/43260; 3.0 kg) and 1,8-diazabicyclo[5.4.0]undec-7-ene (2.3 kg). The mixture was heated to reflux for 3.5 h, allowed to cool to room temperature and quenched by the addition of 2M hydrochloric acid (40 liters). The product was extracted from the acidic aqueous solution with dichloromethane (40 liters) and the organic phase was washed with 2M hydrochloric acid (40 liters) and water (40 liters). The organic phase was concentrated to low volume, diluted with acetonitrile (93 liters) and the resulting suspension heated to reflux. The mixture was allowed to cool and the precipitated product collected by filtration to give the subtitle compound as a white crystalline solid (5.34 kg, 71.3%).

m.p. 184–185° C. $^1$H NMR (300 MHz, CDCl$_3$) δ: 2.40 (s,3H), 3.44 (s, 3H), 3.74 (s, 3H), 3.94 (s, 3H), 5.04 (s, 1H), 5.90 (d, 2H), 6.57 (s, 1H), 6.57–6.73 (m, 3H), 6.87 (d, 1H), 7.04 (s, 1H), 7.22 (d, 1H), 7.64 (dd, 1H), 7.92 (d, 1H), 8.02 (s, 1H), 8.80 (brs, 1H) LRMS: 551.0 (MH$^+$)

(c) 3-{1-(1,3-Benzodioxol-5-yl)-2-[(2-methoxy-4-methylphenyl)sulfonylamino]-2-oxoethyl}-1-methyl-1H-indole-6-carboxylic acid

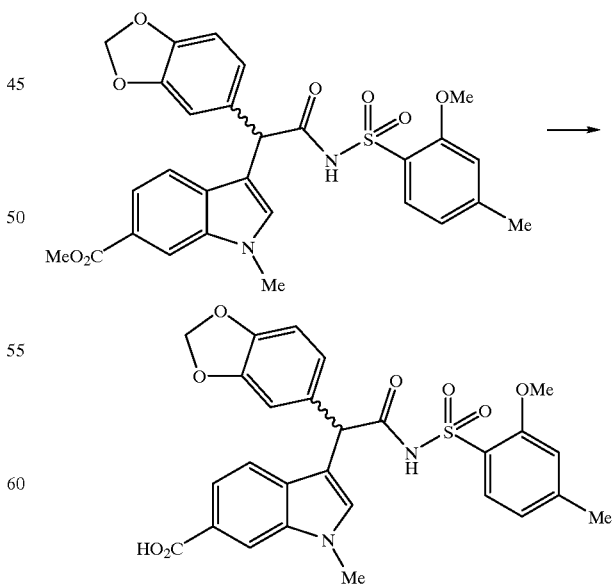

Aqueous sodium hydroxide (9.0 liters of a 20% aqueous solution) was added to a stirred suspension of methyl 3-{1-(1,3-benzodioxol-5-yl)-2-[(2-methoxy4-methylphenyl)-sulfonylamino]-2-oxoethyl}-1-methyl-1H-indole-6-carboxylate (from step (b), 5.0 kg) in methanol (25 liters) and demineralised water (20 liters). The suspension was warmed to 45° C. for 1.5 h, cooled to room temperature and diluted with dichloromethane (25 liters). The pH of the aqueous phase was adjusted to 3 with the addition of concentrated hydrochloric acid (7.0 liters) and the phases separated. The organic phase was concentrated to low volume and filtration of the precipitated product gave the subtitle compound as a white crystalline solid (4.5 kg, 92%).

m.p. 199° C. (DSC) $^1$H NMR (300 MHz, CDCl$_3$) δ: 2.41 (s,3H), 3.40 (s, 3H), 3.75 (s, 3H), 5.07 (s, 1H), 5.92 (d, 2H), 6.51 (s, 1H), 6.68–6.73 (m, 3H), 6.89 (d, 1H), 7.11 (s, 1H), 7.23 (d, 1H), 7.66 (dd, 1H), 7.93 (d, 1H), 8.06 (s, 1H), 9.06 (brs, 1H) LRMS: 537.0 (MH$^+$)

(d) (S)-(+)-3-{1-(1,3-Benzodioxol-5-yl)-2-[(2-methoxy4-methylphenyl)-sulfonylamino]-2-oxoethyl}-1-methyl-1H-indole-6-carboxylic acid

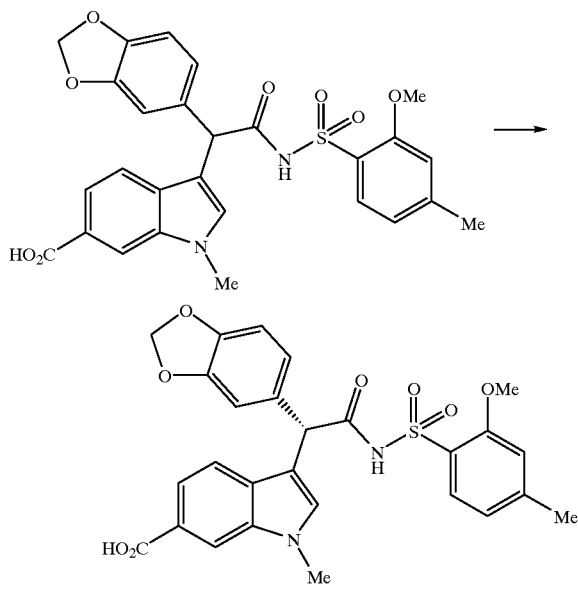

(S)-(−)-α-Methylbenzylamine (0.53 kg) was added over a period of 15 minutes to a stirred suspension of 3-{1-(1,3-benzodioxol-5-yl)-2-[(2-methoxy4-methylphenyl)sulfonylamino]-2-oxoethyl}-1-methyl-1H-indole-6-carboxylic acid (from step (c), 1.17 kg, 2.18 moles) in tetrahydrofuran (6.5 liters, 5.5 ml/g) and 1,2-dimethoxyethane (6.5 liters, 5.5 ml/g) at 60° C. under a nitrogen atmosphere. The resulting solution was allowed to cool to 55° C., seeded with 13.6 g of the (S)-(−)-α-methylbenzylamine salt of the title compound of Example 1 (prepared by conventional methods) and stirred for 24 h. The resulting suspension was allowed to cool to 45° C. over a period of 48 h and stirred at this temperature for an additional 48 h. The suspension was allowed to cool to room temperature and the precipitated (S)-(−)-α-methylbenzylamine salt (of the title compound) collected by filtration (1.316 kg, 84%, ratio of (S)-(−)-α-methylbenzylamine to (S)-(+)-acid in the salt 1.5:1). The salt was partitioned between ethyl acetate (6.8 liters), tetrahydrofuran (1.4 liters) and 1M hydrochloric acid (6.8 liters) and the organic phase was separated and then washed with 1M hydrochloric acid (3×0.9 liters) and water (2×0.7 liters). The organic phase was dried by azeotropic distillation with ethyl acetate at constant volume, concentrated to a volume of 3.5 liters and then n-hexane (3.5 liters) added. The precipitated product was granulated at 0° C. for 1 h and filtered to give the title compound as a white crystalline solid (0.936 kg, 91.6%). The enantiomeric excess of the compound was found to be >94% using chiral stationary phase HPLC.

m.p. 250° C. (DSC) $^1$H NMR (300 MHz, CDCl$_3$) δ: 2.41 (s,3H), 3.40 (s, 3H), 3.75 (s, 3H), 5.07 (s, 1H), 5.92 (d, 2H), 6.51 (s, 1H), 6.68–6.73 (m, 3H), 6.89 (d, 1H), 7.11 (s, 1H), 7.23 (d, 1H), 7.66 (dd, 1H), 7.93 (d, 1H), 8.06 (s, 1H), 9.06 (brs, 1H) LRMS: 537.0 (MH$^+$) Analysis: found C, 60.44; H, 4.47; N, 5.16; $C_{27}H_{24}N_2O_8S$ requires C, 60.43; H, 4.51; N, 5.22%

EXAMPLE 3

Purification of (S-(+-3-{1-(1,3-Benzodioxol-5-yl)-2-[(2-methoxy-4-methylphenyl)-sulfonylamino]-2-oxoethyl}-1-methyl-1H-indole-6-carboxylic acid Sodium hydrogen carbonate (87.3 g, 1.04 moles) was added portionwise to a stirred suspension of (S)-(+)-3-{1-(1,3-Benzodioxol-5-yl)-2-[(2-methoxy-4-methylphenyl)sulfonylamino]-2-oxoethyl}-1-methyl-1H-indole-6-carboxylic acid (from Example 2(d), 279 g, 0.52 moles) in absolute ethanol (0.558 liters) and water (0.558 liters) at room temperature. The suspension was slowly heated to 55–60° C., until all solid had dissolved, diluted with absolute ethanol (2.23 liters) and allowed to cool to room temperature. The precipitated disodium salt was granulated at 0° C. for 2 h and filtered to give a white crystalline solid (0.294 kg, 97.4%). The salt was partitioned between ethyl acetate (1.46 liters), tetrahydrofuran (0.293 liters) and 1M hydrochloric acid (1.46 liters) and the organic phase was separated and then washed with 1M hydrochloric acid (0.293 liters) and water (0.293 liters). The organic phase was dried by azeotropic distillation with ethyl acetate at constant volume, concentrated to a volume of 0.73 liters and then n-hexane (0.9 liters) added. The precipitated product was granulated at 0° C. for 1.5 h and filtered to give the title compound as a white crystalline solid (0.141 kg, 52.5%). The enantiomeric excess of the compound was found to be >99% using chiral stationary phase HPLC.

EXAMPLE 4

The compound of Example 1 was tested in Test A above, and found to have an IC$_{50}$(ET$_A$) which was approximately one quarter that of its enantiomer. Its binding affinity for ET$_A$ receptors (K$_i$) was 4.18 nM, and its selectivity for ET$_A$ receptors over ET$_B$ receptors was approximately 400.

Preparation 1

2-(1,3-Benzodioxol-5-yl)-2-bromoacetic acid

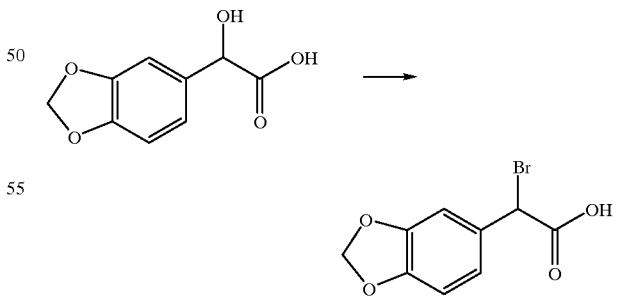

62% Aqueous hydrobromic acid (220 ml) was added slowly to a stirred suspension of 2-(1,3-benzodioxol-5-yl)-2-hydroxyacetic acid (see J Org Chem, 50(23), 4523–6, 1985; 82.4 g) in a mixture of toluene (500 ml) and dichloromethane (1 liter). The mixture was stirred vigorously for 4 h. The aqueous layer was separated and removed and the organics were dried (MgSO$_4$) and concentrated to give a brown oil. The oil crystallised over a 24 h period to give 105.3 g of the title compound.

$^1$H NMR (300 MHz, CDCl$_3$): δ=5.30 (s, 1H), 6.00 (s, 2H), 6.75 (d, 1H), 6.95 (d, 1H), 7.20 (s, 1H).

Preparation 2

2-Methoxy-4-methylbenzenesulfonyl chloride (a) 5-Bromo-2-methoxy-4-methylbenzenesulfonic acid dihydrate

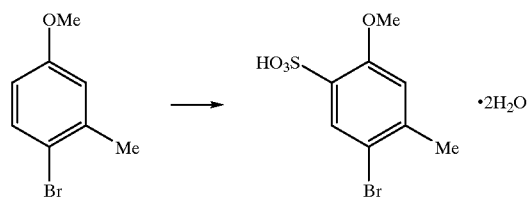

4-Bromo-3-methylanisole (500 g, 2.5 moles) was cautiously added dropwise over a period of 20–25 minutes to 98% sulfuric acid (1,600 ml) at ambient temperature (exothermic, temperature rise to 42–43° C.) and the reaction stirred for 16 hours. The reaction mixture was cautiously quenched onto cooled (0–5° C.) deionised water (7.5 liter) over a 2 hour period at a rate that maintained the temperature below 20° C. The precipitated product was granulated for 3 hours, filtered and dried to give the crude sulphonic acid (980 g). The crude product was recrystallised from ethyl acetate (2.94 liters, 3 ml/g) to give the subtitle compound (680 g, 86% yield) as a white crystalline solid (mp=131–133° C.)

$^1$H NMR (300 MHz, DMSO) δ: 2.29 (s, 3H), 3.72 (s, 3H), 6.97 (s, 1H), 7.74 (s, 1H).

(b) 2-Methoxy-4-methylbenzenesulfonic acid

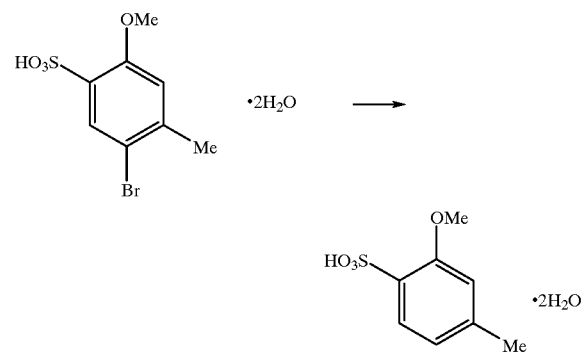

To a solution of 5-bromo-2-methoxy-4-methylbenzenesulfonic acid dihydrate (from (a), 125 g, 0.394 moles) in methanol (1.25 liters, 10 ml/g) was added 5% Palladium on carbon catalyst (12.5 g, 0.1 g/g) and the suspension was hydrogenated at 60° C. and 414 kPa (60 psi) for 16 hours. The reaction mixture was filtered over celite and concentrated to dryness. The crude product was slurried in dichloromethane (250 ml), cooled to 0–5° C. and the subtitle compound (67.5 g, 75% yield) isolated in two crops as a white crystalline solid (mp=92–94° C.) $^1$H NMR (300 MHz, DMSO): δ=2.27 (s, 3H), 3.73 (s, 3H), 6.67 (d, 1H), 6.80 (s, 1H), 7.53 (d, 1H).

(c) 2-Methoxy-4-methylbenzenesulfonyl chloride

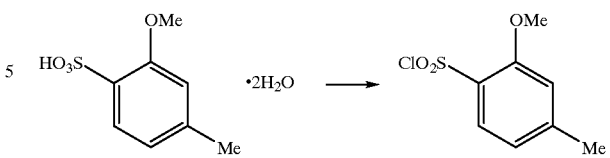

Thionyl chloride (350 ml, 2.5 ml/g) was cautiously added to 2-methoxy-4-methylbenzenesulfonic acid (from (b), 140 g, 0.587 moles) over a period of 30 minutes. The mixture was stirred and heated to reflux for 1 hour and at room temperature for 16 hours. The excess thionyl chloride was removed by evaporation under reduced pressure and the residue was partitioned between deionised water (300 ml) and dichloromethane (400 ml). The phases were separated and the organic phase dried (MgSO$_4$), filtered and concentrated to give the crude product (70 g, 54% yield). The crude product was partially dissolved in hexane (490 ml) at reflux, hot filtered to remove insoluble material and allowed to cool. The precipitated product was collected to give the title compound (41.3 g, 59% recovery) as a white crystalline solid (m.p.=81–84° C.).

$^1$H NMR (300 MHz, CDCl$_3$): δ=2.45 (s, 3H), 4.03 (s, 3H), 6.87–6.90 (m, 2H), 7.82 (d, 1H). LRMS (Thermospray): 238.0 (MNH$_4^+$)

What is claimed is:

1. S-(+)-3-{1-(1,3-Benzodioxol-5-yl)-2-[(2-methoxy-4-methylphenyl)sulfonylamino]-2-oxoethyl}-1-methyl-1H-indole-6-carboxylic acid, which is substantially free from its (R)-(−)-enantiomer, or a pharmaceutically acceptable derivative thereof.

2. A pharmaceutical formulation comprising S-(+)-3-{1-(1,3-benzodioxol-5-yl)-2-[(2-methoxy-4-methylphenyl)sulfonylamino]-2-oxoethyl}-1-methyl-1H-indole-6-carboxylic acid as defined in claim 1, or a pharmaceutically acceptable derivative thereof; in admixture with a pharmaceutically acceptable adjuvant, diluent or carrier.

3. S-(+)-3-{1-(1,3-Benzodioxol-5-yl)-2-[(2-methoxy-4-methylphenyl)sulfonylamino]-2-oxoethyl}-1-methyl-1H-indole-6-carboxylic acid as defined in claim 1, or a pharmaceutically acceptable derivative thereof, for use as a pharmaceutical.

4. A method of treatment of acute renal failure, restenosis or pulmonary hypertension, which comprises administering a therapeutically effective amount of S-(+)-3-{1-(1,3-benzodioxol-5-yl)-2-[(2-methoxy-4-methylphenyl)sulfonylamino]-2-oxoethyl}-1-methyl-1H-indole-6-carboxylic acid as defined in claim 1, or a pharmaceutically acceptable derivative thereof, to a patient in need of such treatment.

5. A process for the production of (S)-(+)-3-{1-(1,3-benzodioxol-5-yl)-2-[(2-methoxy-4-methylphenyl)sulfonylamino]-2-oxoethyl}-1-methyl-1H-indole-6-carboxylic acid as defined in claim 1, or a pharmaceutically acceptable derivative thereof, which comprises selective precipitation from a solution of 3-{1-(1,3-benzodioxol-5-yl)-2-[(2-methoxy-4-methylphenyl)sulfonylamino]-2-oxoethyl}-1-methyl-1H-indole-6-carboxylic acid of a diastereomeric salt formed between (S)-(+)-3-{1-(1,3-benzodioxol-5-yl)-2-[(2-methoxy-4-methylphenyl)sulfonylamino]-2-oxoethyl}-1-methyl-1H-indole-6-carboxylic acid and a chiral base.

6. A process as claimed in claim 5, wherein the chiral base is (S)-(−)-α-methylbenzylamine.

7. A process as claimed in claim 5, wherein the solvent is a mixture of tetrahydrofuran and 1,2-dimethoxyethane.

8. A process as claimed in claim 5, wherein the diastereomeric salt is formed by mixing the acid with the base in a molar ratio in the range 1:1.5 to 1:2.5.

9. A process as claimed in claim 5, wherein the temperature is initially in the range 55–60° C., and then reduced to 45° C.

10. A process as claimed in claim 9, wherein the temperature reaches 45° C. 3 days after beginning the process.

11. A process as claimed in claim 5, wherein 10 ml of solvent is used for every gram of acid present.

12. A process as claimed in claim 5, wherein the reaction mixture is seeded with the desired diastereomeric salt.

13. A process for the production of S-(+)-3-{1-(1,3-benzodioxol-5-yl)-2-[(2-methoxy4-methylphenyl)sulfonylamino]-2-oxoethyl}-1-methyl-1H-indole-6-carboxylic acid as defined in claim 1, or a pharmaceutically acceptable derivative thereof, which comprises removing the protecting group from the (+)-enantiomer of a compound of formula I, which is substantially free from its (−)-enantiomer,

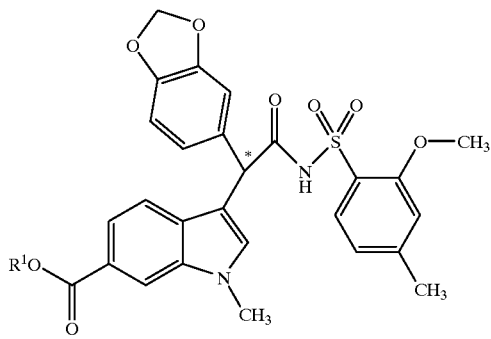

I wherein $R^1$ represents a carboxylic acid protecting group.

14. A process for the production of the (+)-enantiomer of a compound of formula I, as defined in claim 13, which comprises reacting 2-methoxy-4-methylbenzenesulfonyl chloride with the (−)-enantiomer of a compound of formula II, which is substantially free from its (+)-enantiomer,

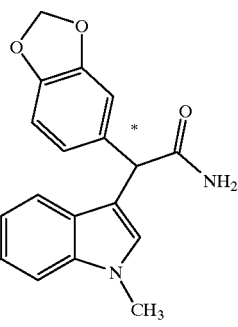

II wherein $R^1$ is as defined in claim 13.

15. The (+)-enantiomer of a compound of formula I, as defined in claim 13.

16. The (−)-enantiomer of a compound of formula II, as defined in claim 14.

\* \* \* \* \*